United States Patent
Keller et al.

(10) Patent No.: US 6,876,759 B2
(45) Date of Patent: Apr. 5, 2005

(54) IMAGE TRANSMITTING SYSTEM, IMAGE TRANSMITTING METHOD AND STORAGE MEDIUM

(75) Inventors: Scott Keller, Mount Prospect, IL (US); Kaushal Shastri, Stamford, CT (US); Renee Walsh, Wilton, CT (US)

(73) Assignees: Fuji Photo Film Co., Ltd., Kanagawa-ken (JP); Fujifilm Medical Systems U.S.A., Inc., Stamford, CT (US)

( * ) Notice: Subject to any disclaimer, the term of this patent is extended or adjusted under 35 U.S.C. 154(b) by 458 days.

(21) Appl. No.: 09/773,248

(22) Filed: Feb. 1, 2001

(65) Prior Publication Data

US 2002/0102012 A1 Aug. 1, 2002

(51) Int. Cl.[7] .................................................. G06K 9/00
(52) U.S. Cl. ........................ 382/128; 382/305; 358/403
(58) Field of Search .................................. 382/128, 129, 382/130, 131, 132, 133, 134, 181, 224, 226, 276, 282, 295, 305, 306; 378/165, 28, 29, 62; 703/3; 709/219, 220; 358/403, 1.14, 1.15, 404; 345/618, 619; 348/49, 54

(56) References Cited

U.S. PATENT DOCUMENTS

| | | | | | |
|---|---|---|---|---|---|
| 5,384,643 | A | * | 1/1995 | Inga et al. | 358/403 |
| 5,502,576 | A | * | 3/1996 | Ramsay et al. | 358/444 |
| 6,112,234 | A | * | 8/2000 | Leiper | 709/219 |
| 6,381,029 | B1 | * | 4/2002 | Tipirneni | 358/1.14 |
| 6,396,941 | B1 | * | 5/2002 | Bacus et al. | 382/128 |
| 6,513,035 | B1 | * | 1/2003 | Tanaka et al. | 707/3 |
| 6,542,579 | B1 | * | 4/2003 | Takasawa | 378/165 |

\* cited by examiner

*Primary Examiner*—Bhavesh M. Mehta
*Assistant Examiner*—Seyed Azarian
(74) *Attorney, Agent, or Firm*—Sughrue Mion, PLLC

(57) ABSTRACT

In an image transmitting system comprising an image server and a display terminal, transmission of image data for use in remote diagnosis is simplified. A communications circuit having a low data transmission rate, such as a telephone line, connects the image server and display terminal. From the display terminal, the subscription of a folder, based on the predetermined subscription conditions, is specified to the image server. The image server classifies image data satisfying the subscription conditions into a folder and manages it. When new image data satisfying the subscription conditions is stored in the image server, notification thereof and/or said new image data is transmitted to the display terminal.

8 Claims, 5 Drawing Sheets

IMAGE TRANSMITTING SYSTEM, IMAGE TRANSMITTING METHOD AND STORAGE MEDIUM

BACKGROUND OF THE INVENTION

1. Field of the Invention

The present invention relates to an image transmitting system, image transmitting method and storage medium, and in particular to a computer executable program stored on computer readable recording medium for transmitting image data from a remote image server to a display terminal via a network according to the image transmitting method of the present invention.

2. Description of the Related Art

There are in use in the medical field today apparatus (modalities) for forming X-ray and other diagnostic images used in a variety of diagnosis, including CR (computed Radiography) apparatus, CT (Computerized Tomography) apparatus, MRI (Medical Resonance Imagery) apparatus, etc. The image data produced in each modality is displayed on a CRT terminal (hereinafter referred to simply as a CRT), or output by a laser printer, etc. to film, etc. for use by a reader at a medical treatment site in ascertaining the presence or absence of a disease, tissue damage, etc.

In addition, recent advances in computer and communications technology have seen the deployment of medical network systems (hereinafter referred to simply as networks) in hospitals and other facilities. Therefore, whereas in the past the aforementioned modalities were used only on a stand-alone basis, now they are connected to a network as image input apparatus, and CRTs, laser printers, etc., as image output apparatus.

Aside from aforementioned image input and output apparatus, also connected to such a network is an image server equipped with recording means for recording image data output by the image output devices, as it is, or after it has been subjected to a predetermined data-compression process, to a storage medium such as a hard disk, a RAID (Random Array of Inexpensive Disks), an optical disk: CD-R, DVD, DLT (Digital Linear Tape); etc. Image data input to such an image server is temporarily recorded on a high output-speed temporary storage medium such as a hard disk or a RAID, and after the specified conditions have been satisfied (such as the passage of a predetermined period of several weeks to several months after a doctor has completed diagnosis employing an image), the image data is compressed and recorded on a recording medium such as an optical disk, etc. (archive), for semi-permanent storage. Furthermore, data management of image data thus stored in the image server, such as transferring image data from a temporary storage medium to an archive, etc. is conducted by a database.

In such a network, predetermined image data is transmitted from the image server to a workstation connected to the network in response to a request from the workstation. In addition, not only the internal network of a hospital, but also a computer at a doctors residence, for example, can be connected via a communications circuit such as a telephone line to enable image data to be read out from the image server in order to carry out so-called remote diagnosis (teleradiology).

However, compared to the dedicated lines composing the internal hospital network, data transmitted over aforementioned communications circuits is transmitted at a slower rate, and therefore the time required for downloading image data is longer. In order to improve transmitting efficiency of diagnostic images to be utilized for remote diagnosis, it is proposed to provide for transmission of image data that has been determined in advance to be the desired image data and which has been subjected to a comparatively high-rate data-compression process, and to provide notification upon completion of transmission, using the so-called push-style.

Transmission of image data in remote diagnosis as described above is performed in response to the issuance of a request by a Doctor A, and after the image data has been transmitted, the same image data exists on both the doctor's computer and the image server. Under such circumstances, for cases in which transmitted image data is to be compared to other image data (image data taken in the past, for example), or when another, different image data is to be transmitted, a software application is required to keep track of what image data has been transmitted to a doctors computer, and manage the transmission of image data so as to prevent retransmission of image data that already exists in the doctors computer, etc. However, because a high degree of complexity is required in a software application for managing transmission of image data, development of such an application program would require a large amount of time and effort.

On the other hand, when performing remote diagnosis it is also possible for a doctor to access the image server from his or her computer, and download and view the required images. However, when accessing the server to examine image data, because the doctor must first find the desired image data, the efficiency of diagnosis is reduced and longer connection times are required.

SUMMARY OF THE INVENTION

The present invention has been developed in consideration of the problems described above. The object of the image data transmitting system of the present invention is to provide a computer-executable application recorded on a computer-readable storage medium that causes a computer to execute the image data transmitting method according to the present invention, whereby management of the transmission of image data is simplified.

The image transmitting system according to the present invention has an image server and a display terminal connected by a network, wherein the image server is provided a function that enables it to classify image data according to the predetermined subscription conditions and to create at least one folder, and when new image data satisfying the predetermined subscription conditions is stored in the image server, the image server provides notification thereof, and/or the new image data is transmitted to aforementioned display terminal.

The expression "predetermined subscription conditions" refers to the conditions necessary to be fulfilled for image data to be classified into a folder to be created. More specifically, such conditions can include a condition stating that image data from a specific examination be classified into a given folder; a condition stating that the image data of a particular series of image data from a specific examination be classified into a given folder; a condition stating that image data acquired for a patient who has a specified doctor in charge of his or her care be classified into a given folder, and any of the various conditions which can be specified by a doctor from the display terminal. Further, the word "series" here refers to the separate items examined in a specific examination. Take for example, a case in which an examination has been conducted employing CT images, the series refers to the separate CT images, such as "CT head image", "CT chest image", etc.

The word "folder" refers to the storage unit having a kind of filtering function for classifying image data according to the predetermined subscription conditions. For example, if aforementioned predetermined subscription condition states that image data from a specific examination is to be classified into folder A, the image data from the specific examination is classified into folder A. Note that it is possible to have the image data actually stored in the folder, however, it is also possible to have the image displayed for examination upon opening of the folder.

The expression "new image data is stored" refers to the notification provided to the user of a display terminal that new image data satisfying the predetermined subscription conditions of a desired folder has been stored in the image server. More specifically, a text message reading, "New image data has been stored" or words to that effect, or voice notification may be employed to provide notification to the display terminal. Note that "notification" refers to the data transmitted to the display terminal by the image server indicating that new image data has been stored, and may be displayed on the display terminal as text, rendered as voice notification, etc. In addition, a system in which flags can be set for indicating that new image data has been stored can be employed for notification. In such a system, the display terminal periodically accesses the image server at set intervals and confirms whether or not any flags have been set. For cases in which the presence of flags at the image server is confirmed, notification thereof is displayed, etc. at the display terminal. In this case, accessing of the image server by the display terminal is not limited to such periodical accessing at set intervals, but can include instances when a user of a terminal runs a software program (a Web browser, for example) to access the image server, instances in which the image server is accessed to conduct a search for image data, etc.

The expression "new image data is acquired" refers to new image data that can be displayed on a user's display terminal when new image data satisfying the predetermined subscription conditions of a desired folder has been stored. More specifically, when new image data is stored in the image server, said new image data may be transmitted from the image server to the display terminal, and the display terminal thereby acquires the new image data. In addition, flags for indicating that new image data has been stored in the image server can be set, and the display terminal access the image server periodically at set intervals to confirm whether or not any flags have been set; for cases in which there are flags set, the display terminal issues a request to the image server for transmission of the new image data, and the new image data is transferred and received by the display terminal, and thereby acquired. In this case, accessing of the image server by the display terminal is not limited to such periodical accessing at set intervals, but can include instances when a user of a terminal runs a software program (a Web browser, for example) to access the image server, or instances in which the image server is accessed to conduct a search for image data, etc. Further, new image data may be acquired by a display terminal by the image transmission of new image data by the image server in response to a request issued by a user of a display terminal to the image server. Note that new image data acquired by the display terminal may be stored in a storage medium at the display terminal, such as a temporary buffer memory, a hard disk, etc.

Note that if accompanying issuance of notification, the new image data is also transmitted to and thereby acquired by the display terminal, the new image data may be displayed on the display terminal immediately.

According to the image transmitting method of the image transmitting system comprising an image server and a display terminal according to the present invention, the image server classifies image data according to the predetermined subscription conditions and creates at least one folder for managing said image data, the subscription conditions for the desired folder are set at the display terminal, and when new image data satisfying the subscription conditions is stored in the image server, notification thereof is provided to the display terminal, and/or the new image is transmitted to and thereby acquired by the display terminal.

Note that the present invention may also be provided as a software application recorded on a computer-accessible storage medium that causes each of the steps of the image data transmitting method of the present invention to be executed by a computer.

The image server of the image transmitting system of present invention comprising an image server and an image terminal connected by a network is provided a function for classifying image data according to the predetermined subscription conditions and creating at least one folder for managing said image data.

The display terminal of the image transmitting system of present invention comprising said image server and an image terminal connected by a network specifies the subscription of a desired folder among the, at least one, folders created in the image server, for classifying, according to the predetermined subscription conditions, and managing said image data, and is provided a function for, when new image data satisfying the predetermined subscription conditions of aforementioned desired folder has been stored in the image server, acquiring notification thereof and/or said new image data.

In another image transmitting system of the present invention comprising an image server and a display terminal connected by a network: the image server is provided a function for classifying image data according to the predetermined subscription conditions and creating at least one folder for managing said image data; the display terminal is provided a function for specifying the subscription of the desired folder, and for cases in which new image data has been stored in said desired folder, acquiring notification thereof and/or said new image data.

In another image transmitting system of the present invention comprising an image server and a display terminal connected by a network: data is classified according to the predetermined subscription conditions and at least one folder is created in the image server for managing said image data; the subscription of the desired folder is specified at the display terminal, and for cases in which new image data has been stored in said desired folder, notification thereof and/or said new image data is acquired by the display terminal.

Note that these alternative versions of the image transmitting method according to the present invention may also be provided as a software application recorded on a computer-accessible storage medium that causes each of the steps of these alternative image data transmitting methods to be executed by a computer.

In another image server of the image transmitting system of present invention comprising said image server and an image terminal connected by a network, said image server is provided a function for classifying image data according to the predetermined subscription conditions and creating at least one folder for managing said image data.

In another display terminal of the image transmitting system of the present invention comprising an image server and said image terminal connected by a network, said display terminal is provided a function for specifying the subscription of a desired folder among the at least one folders created in the image server, for managing said image data, by classifying image data according to the predetermined subscription conditions, and for cases in which new image data satisfying the predetermined subscription conditions of aforementioned desired folder has been stored in the image server, acquiring notification thereof and/or said new image data.

According to the present invention, image data is classified according to the predetermined subscription conditions and at least one folder is created in the image server for managing said image data, and the subscription of a desired folder is specified at the display terminal. Because of this, by only accessing the server from the display terminal and opening the desired folder to view the image data meeting the predetermined subscription conditions, thereby eliminating the need for developing a complex system for managing image data transmission. In addition, because notification of the fact that new image data satisfying the predetermined subscription conditions has been stored ad/or said new image data is acquired by the display terminal when new image data is stored, the need to search from the display terminal for image data acquired by the server is eliminated, server access time is reduce, and image data can be examined in a more effective manner.

In addition, because for cases in which new image data has been stored in a desired folder, notification thereof and/or said new image data is acquired by the display terminal, the need to search from the display terminal for image data acquired by the server is eliminated, server access time is reduce, and image data can be examined in a more effective manner.

DESCRIPTION OF THE PREFERRED EMBODIMENT

A preferred embodiment of the present invention will now be described with reference to the drawings.

Figure 1:
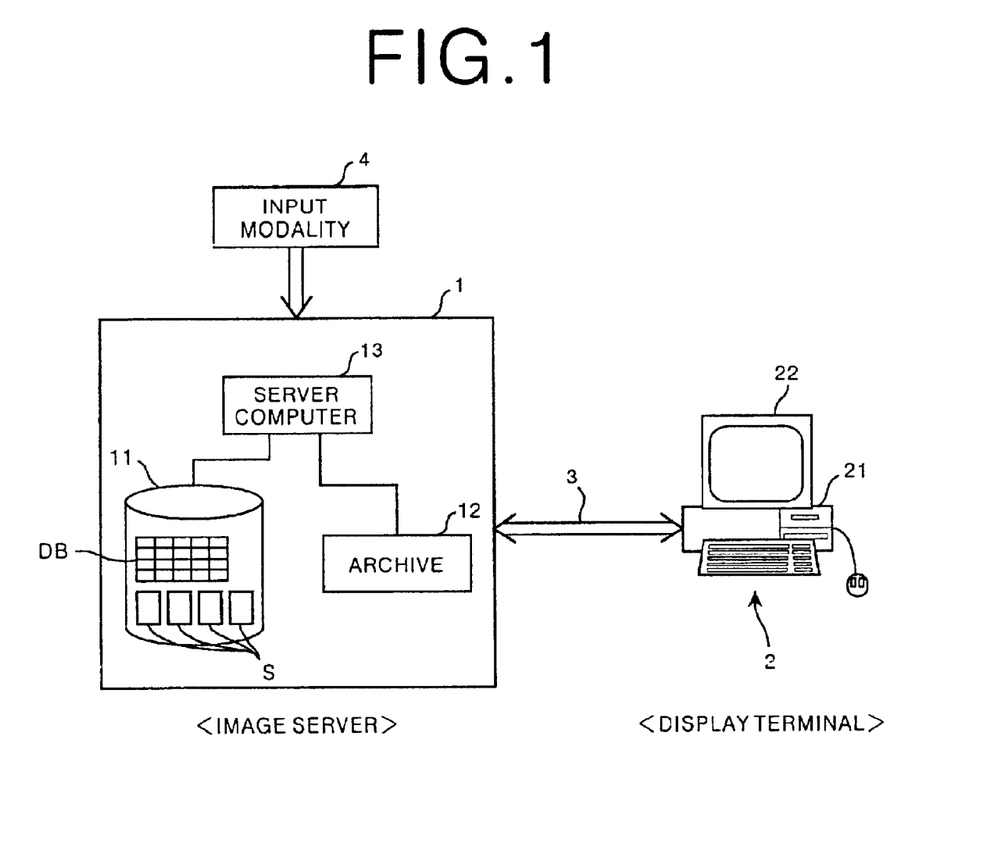
FIG. 1 is a schematic block drawing showing the configuration of the image transmitting system of the present invention.

FIG. 1 is a schematic block diagram depicting the configuration of the image transmitting system according to the present invention. As shown in FIG. 1, the image transmitting system of a preferred embodiment of the present invention comprises an image server 1 storing image data S, and a display terminal 2, which is a computer at a doctor's residence, etc. connected by a communications circuit 3 having a comparatively low data transmission rate. In addition, image server 1 is also connected to the hospitals internal medical network (not shown).

Image server 1 is provided with: a temporary storage medium 11, such as a RAID (Redundant Array of Inexpensive Disks), etc. for temporarily storing image data S; an archive disk 12, such as a CD-R, DVD, DLI, etc. for providing semi-permanent storage of image data S after a specified period of time has elapsed; and a server computer 13 for controlling various operations and processes of image server 1. Further, image server 1 is connected to an input modality 4 such as CR apparatus, CT apparatus, MRI apparatus, etc., from which it receives formed image data S, which it stores and manages. In this way, image data S, as well as a database DB containing the information stored on temporary storage medium 11 and archive disk 12, are stored on temporary storage medium 11.

Display terminal 2 is installed at a doctor's residence, and is equipped with a personal computer 21 and a CRT, LCD, etc. monitor 22. Additionally, personal computer 21 has installed on it a web browser commonly available on the market such as Internet Explorer (registered trademark of Microsoft Inc.), by which access to image server 1 via communications circuit 3 is provided, and image data S stored on temporary storage medium 11 can be stored in a temporary buffer memory of the web browser and viewed. Note that normally only image data S stored on the temporary storage medium 11 can be viewed at display terminal 2. For cases in which it is necessary to view image data S stored on archive disk 12, it is necessary to first contact the hospital at which the image server is housed and have image data S stored on the archive disk 12 copied to temporary storage medium 11.

Note that, according to the conditions specified (upon the passing of a predetermined period of time after diagnosis by a doctor has been performed, for example), image data S is copied from temporary storage medium 11 to archive 12. For example, when said specified conditions are satisfied, the exact same image data S as that stored in temporary storage medium 11 is copied to archive 12, and as the amount of storage space on temporary storage medium 11 becomes unavailable for use, said image data S is deleted from temporary storage medium 11 in the order commencing from the oldest date thereof, whereby it becomes stored exclusively in archive 12. Note that according to the purpose of image data S, it may be compressed and stored in both temporary storage medium 11 and archive 12. In addition, original image data or original image data that has been compressed and is extractable can be stored in temporary storage medium 11, and when said image data is copied to archive 12 it can be compressed non-reversibly.

Further, copying data S to archive 12 and deleting data S from temporary storage medium 11 are managed by the database DB. Accordingly, if a request for image data S that has been deleted from temporary storage medium 11 is issued by display terminal 2, said image data is read out from archive 12 and transmitted to display terminal 2. In this case, although more time is required for such reading out and transmitting from archive 12, compared to cases in which image data S is transmitted to display terminal 2 from temporary storage medium 11, the image represented by image data S can be displayed by display terminal 2 without recognition of the storage location of said image data S.

Image server 1 classifies image data S into a folder according to the predetermined subscription conditions. The folder can be created by a command issued by display terminal 2, or in the image server, and aforementioned predetermined subscription conditions can be set for each folder. The predetermined subscription conditions are the conditions for classifying image data S into a created folder. For example, a condition stating that the image data S for a specific examination be classified into a created folder, a condition stating that a particular series of image data S be classified into a created folder, or for cases in which image data has been acquired for a patient whom is under the care of Doctor A, a condition stating that said image data S be classified into a created folder, etc., may be employed as predetermined subscription conditions.

Image server 1 classifies the data S stored on temporary storage medium 11, based on the predetermine subscription conditions, into a folder and manages it. Therefore, for cases in which a condition stating that CT images are to be stored in a given folder has been set, image data S representing CT images is classified into that folder. The classification may consist of the actual storing of said image data in said folder, or it may consist of having the image(s) represented by said image data displayed for viewing on display terminal 2 upon opening said folder.

In addition, when new image data S that satisfies the predetermined subscription conditions of a folder created in image server 1 is stored, notification thereof is provided to the doctor who is the user of image display terminal 2. More specifically, a data representing a line of displayable text reading, "A new image has been stored," or words to that effect is transmitted to display terminal 2 and displayed on monitor 22, whereby notification is provided to the doctor who is the user of image display terminal 2. Further, flags indicating that new image data has been stored in image server 1 can be set. Display terminal 2 accesses image server 1 periodically at set intervals to confirm whether or not any such flags have been set, and for cases in which flags have been set, a line of text reading, "A new image has been stored," or words to that effect can be displayed on display terminal 2 as notification that new image data S has been stored. Additionally, in place of the text message, a voice notification method may be employed to provide notification that new image data S has been stored.

Then, by issuing a request for transmission of new image data S to image server display terminal 2 can acquire said image data S.

Note that new image data S acquired by display terminal 2 may be stored in a temporary buffer memory managed by the Web browser, the hard disk of display terminal 2 or in both the temporary buffer memory and the hard disk.

In this way, after a doctor confirms the notification that new image data S has been stored, the image represented by new image data S can be viewed at display terminal 2 immediately.

Note that for cases in which the flags described above have been set, a request for immediate transmission of said new image data S from image server 1 can be issued by display terminal 2.

Figure 2:
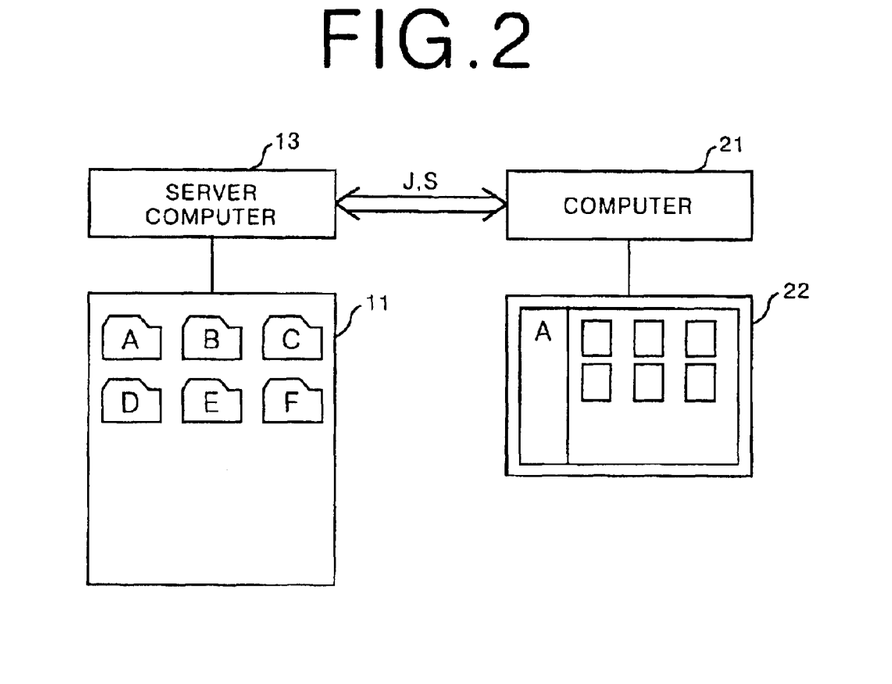
FIG. 2 is a block drawing showing the operation of the preferred embodiment
Figure 3:
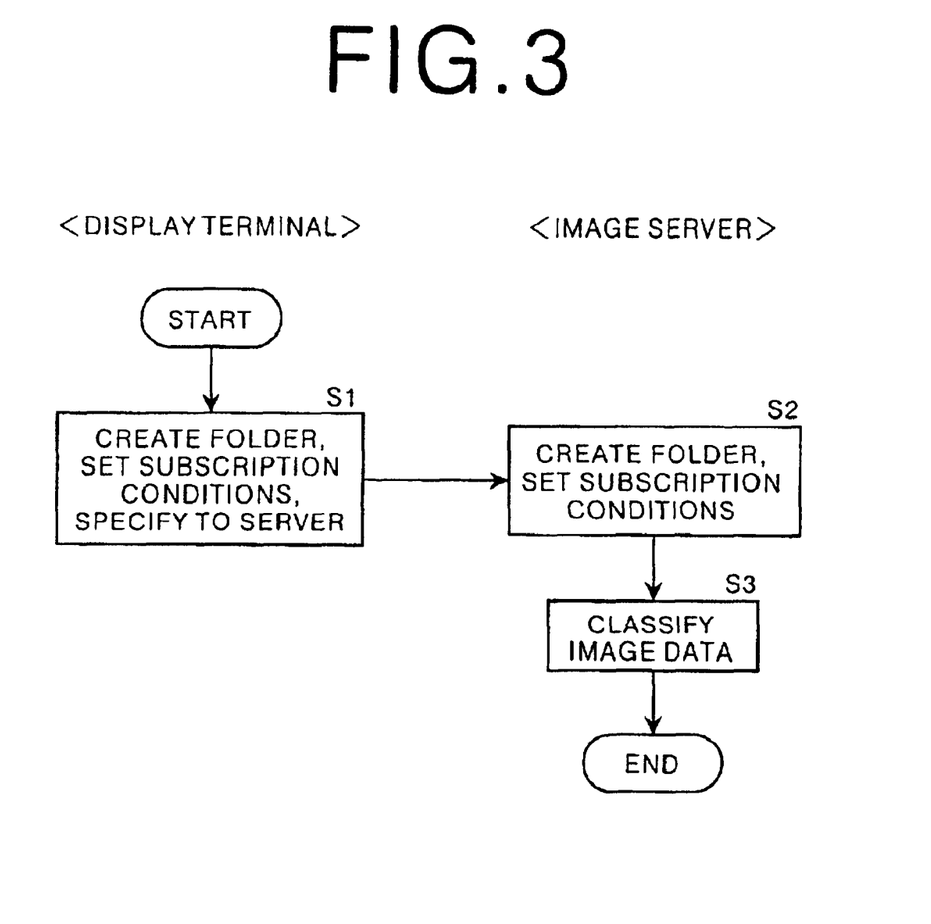
FIG. 3 is a flowchart showing the operation of the preferred embodiment through classification processing.
Figure 4:
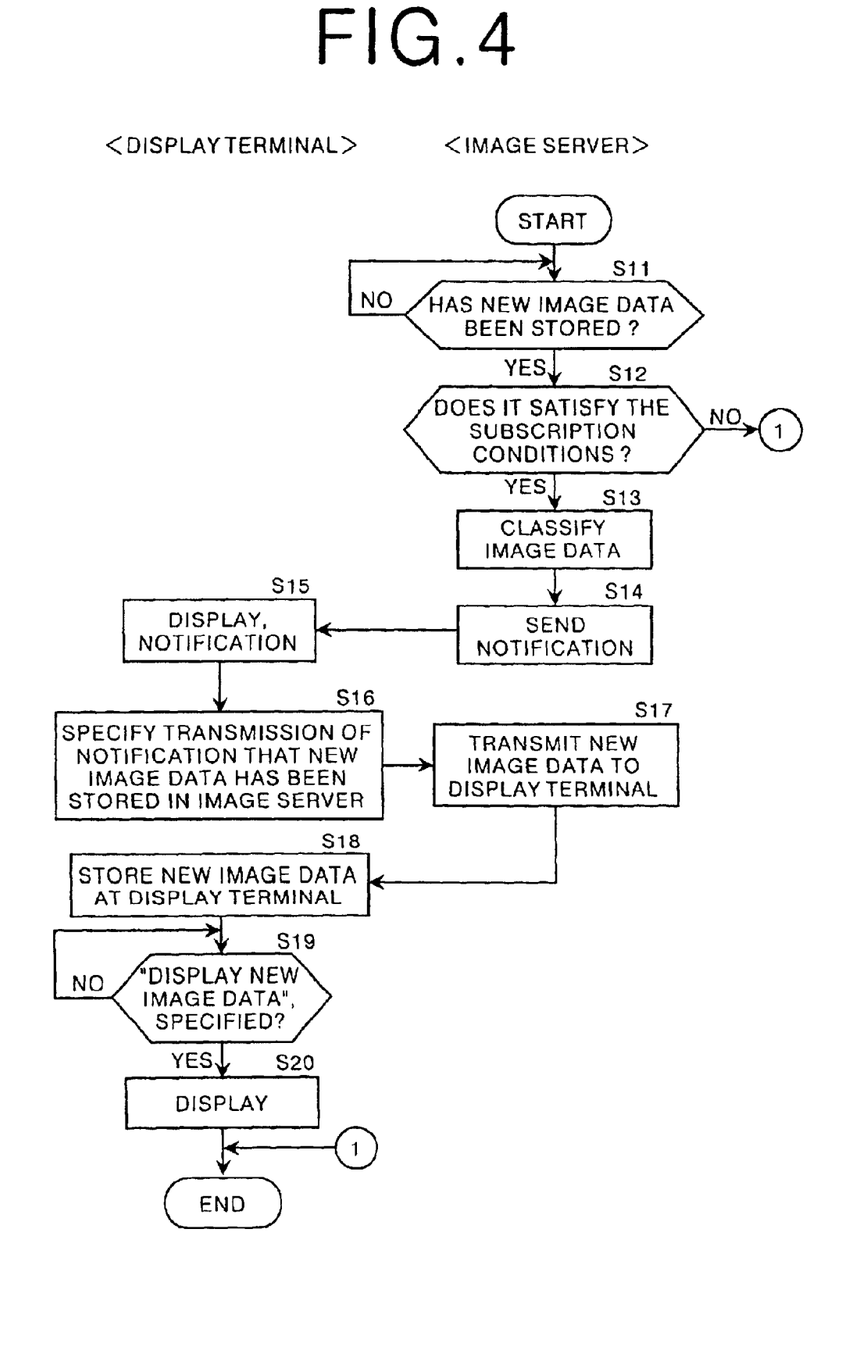
FIG. 4 is a flowchart showing the processing of newly acquired image data in the preferred embodiment.

Next, the operation of the current embodiment will be explained. FIG. 2 is a block drawing to which reference will be made in explaining the operation of the current embodiment. FIG. 3 is a flowchart showing the processing of the image data S up to classification. FIG. 4 is a flowchart showing the image classification process for new Image data. For the sake of simplicity, only the temporary storage medium 11 and the server computer 13 are shown for the illustration of image server 1 in FIG. 2.

First, from display terminal 2, using the web browser, the settings of the subscription conditions are specified (Step S1) Image server 1 receives the specification from display terminal 2, creates the folder specified and sets the subscription conditions to the folder (Step S2). Six folders have been created in the current embodiment, and subscription conditions have been set for each folder, as in for example, "Image data for patients of Doctor A are to be classified into folder A." Then, according to the subscription conditions set, image data S is classified into folders (Step S3), and the processing is thereby completed. In this way, the image data for patients of Doctor A are classified into folder A and managed. However, for cases in which there is no image data S that satisfies the subscription conditions, the processing is completed without any classifying having been performed.

Next, the processing that takes place when new image data is stored in image server 1 will be explained. In the image server 1, the status as to whether or not new image data has been stored in temporary storage medium 11 from input modality 4 is monitored regularly (Step S11). When newly stored image data registers "Yes" in Step 11, an evaluation of said new image data S is conducted to determine if it satisfies the subscription conditions of a given folder (Step S12). If the new image data S is found in Step S12 not to satisfy the subscription conditions, it is stored in temporary storage medium 11, and the processing is thereby complete. On the other hand, if in Step S12 the new image data is found to satisfy the subscription conditions, it is classified accordingly into the proper folder (Step S13). After classification has been completed, data representing the fact that new image data has been stored in image server 1 is transmitted to display terminal 2 (Step S14).

When said data is received by display terminal 2, the gist of the message is displayed on monitor 22 and the doctor who is the user of said display terminal 2 is thereby provided notification that new image data has been stored in image server 1 (Step S15). Accompanying this, a request for transmission of said new image data S is issued to image server 1 by display terminal 2 (Step S16). Accordingly, image server 1 transmits new image data S to display terminal 2 (Step S17). Display terminal 2 stores received new image data S in a temporary buffer memory, etc. (Step S18).

Then, a check is performed to determine whether or not new image data S has been specified to be displayed (Step S19), and if in Step S19 new image data is found to have been specified to be displayed, said new image data S is displayed on monitor 22 (Step S20), and the processing is complete.

More specifically, when new image data S1 for a patient of Doctor A is newly stored in image server 1, said new image data S1 is classified into folder A, notification thereof is sent to Doctor A's display terminal 2, and additionally, new image data S1 is transmitted to display terminal 2 and displayed on monitor 22.

Note that it is also possible for Doctor A at display terminal 2 to access image server 1 using the web browser following said notification, open the folder into which new image data S has been classified, and view image data S satisfying the subscription conditions and new image data S1, on monitor 22.

Because in the current embodiment, folders are created in image server 1, and the subscription conditions for said folder are set, image data satisfying said subscription conditions is classified into folders and managed in image server 1. In this way, by only opening a folder at display terminal 2, image data S of the requested subscription can be viewed at display terminal 2, and the need for complicated administration and control of transmission of image data S is thereby eliminated.

Moreover, when new image data satisfying the subscription conditions is stored, because notification thereof is provided to and said image data S is transmitted to display terminal 2, the need to search at display terminal 2 for image data S acquired by image server 1 is eliminated, server access time is reduced and examination of images can be performed in a more efficient manner.

Here, for cases in which the specified ID number of a patient whom image data has been acquired of is incorrect, or the data appended to image data S by image server 1 is found to be incorrect and any other such cases in which image data S is found to have irregularities, it is advantageous to have said image data S having irregularities classified into a folder created in image server 1. In this way, if the subscription of such a folder is left specified on the terminal of the manager of the image transmitting system (system administrator), it becomes easy for the system administrator to know that image data S having irregularities has been stored on image server 1.

Note that, whereas in the embodiment described above, notification that new image data has been stored is transmitted to the doctor who is the user of display terminal 2, it is also possible to not provide notification and instead, to have said new image data transmitted to the display terminal 2.

In addition, although new mage data is classified into a folder in the embodiment described above, in input modality 4, a plurality of image data S is formed for each examination, or for each series of an ongoing examination. For such cases, in order that said plurality of new image data S is classified into folders, notification that new image data S has been stored and/or said new image data is acquired by display terminal 2 for each examination or series.

Further, in the embodiment described above, when new image data S is stored in image server 1, said new image data is classified into a folder, however, it is also possible for the operator of a image server 1 to store new image data into a folder manually. Additionally, image data may be stored manually in a folder (for which Doctor A has set the subscription conditions, for example) specified by the user of a given terminal (the X-ray technician's terminal, for example). For such cases, when new image data S is stored in said folder, notification thereof and/or said new image data is acquired by the display terminal 2 subscribing to said folder. Hereinafter, this will be explained as another embodiment.

Figure 5:
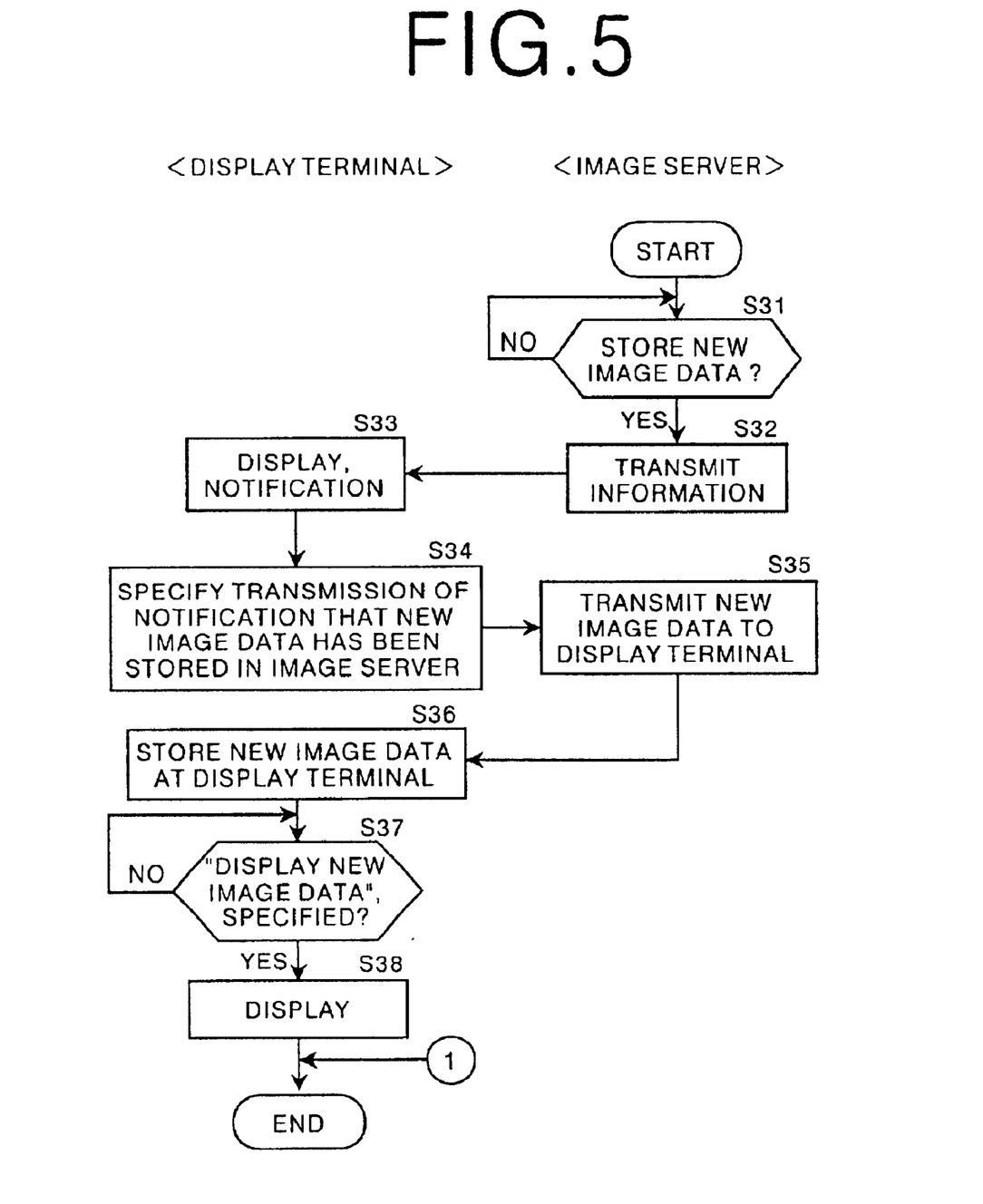
FIG. 5 is a flowchart showing another operation of preferred embodiment of the present invention.

FIG. 5 is a flowchart showing the operation of another embodiment of the present invention. A given folder created in image server 1 is monitored regularly to ascertain whether or not new image data has been stored therein or not (Step S31), and if a "yes" is registered in Step 31, data representing the fact thereof is transmitted to display terminal 2.

When display terminal 2 receives transmission of said data, it displays the gist thereof and the user of display terminal 2 is thereby provided notification that new image data S has been stored in said folder (Step S33). Accompanying this, display terminal 2 issues to image server 1 a request for transmission of said new image data S (Step S34). Accordingly, image server 1 transmits the new image data S to display terminal 2 (Step S35). Display terminal 2 receives said transmission and stores new image data S in a temporary buffer memory, etc. (Step S36).

Then, a check is performed to determine whether or not new image data S has been specified to be displayed (Step S37), and if a "yes" is registered in Step S37, the new image data is displayed on monitor 22 (Step S38), and the processing is completed.

More specifically, for cases in which image data S1 for a patient of Doctor A s stored in a folder whose subscription conditions are specified by Doctor A, notification that new image data S1 has been stored in said folder is provided to Doctor A's display terminal 2, and said image data is transmitted to said display terminal 2 and displayed on monitor 22.

In this way, the need to search from display terminal 2 for image data stored in image server 1 is eliminated, server access time is reduced, and image data S1 can be viewed in a more effective manner.

What is claimed is:

1. An image transmitting system for transmitting images over a network comprising:
   an image server; and
   a display terminal; wherein
   said image server and said display terminal communicate;
   said image server is provided with the capability of classifying image data according to predetermined subscription conditions and creating at least one folder for managing said image data, where said predetermined subscription conditions may be initiated from any computer;
   said display terminal specifies a subscription to a desired folder in said image server and periodically checks said image server for newly arrived image data saved in said desired folder; and
   when newly arrived image data satisfying the predetermined subscription conditions of said desired folder has been stored in the image server, said display terminal acquires information that said newly arrived image data is stored in said image server and either generates notification thereof and/or acquires said newly arrived image data.

2. An image transmitting method for an image server and a display terminal connected via a network, said method comprising:
   initiating predetermined subscription conditions, where said predetermined subscription conditions may be initiated from any computer; and
   creating at least one folder for managing said image data; and
   providing said display terminal with functions for specifying a subscription to a desired folder and for periodically checking said desired folder such that when newly arrived image data satisfying the predetermined subscription conditions or said desired folder has been stored in the image server, said display terminal acquires information that said newly arrived image data is stored in said image server and either generates notification thereof and/or acquires said newly arrived image data.

3. A computer program product containing program code for causing a computer to perform the method of claim 2.

4. An image transmitting system for transmitting images over a network comprising:
   an image server; and
   a display terminal; wherein
   said image server and said display terminal communicate;
   said image server is provided with classifying means for classifying image data according to predetermined subscription conditions and creation means for creating at least one folder for managing said image data, where said predetermined subscription conditions are initiated from any computer; and
   said display terminal is provided with both specifying means for specifying a subscription to a desired folder stored in said image server and checking means for checking said desired folder for newly arrived image data; and when newly arrived image data satisfying the predetermined subscription conditions of said desired folder has been stored in the image server, said display terminal instigates acquisition means for acquiring information specifying that said newly arrived image data is stored in said image server and either generates notification thereof and/or acquires said newly arrived image data.

5. The system of claim 1, wherein said display terminal acquires information on said newly arrived image data automatically.

6. The method of claim 2, wherein said periodically checking said desired folder occurs automatically.

7. The computer program product of claim 3, wherein said periodically checking said desired folder occurs automatically.

8. The image transmitting system of claim 4, wherein said display terminal automatically instigates said acquisition means.

* * * * *